United States Patent [19]
Reed et al.

[11] Patent Number: 5,548,075
[45] Date of Patent: Aug. 20, 1996

[54] DNA CASSETTE AND TRANSGENIC ORGANISMS CARRYING LYTIC PEPTIDE-ENCODING GENES

[75] Inventors: William A. Reed, Benson; Kenneth L. White, North Logan, both of Utah

[73] Assignee: Utah State University, Logan, Utah

[21] Appl. No.: 114,692

[22] Filed: Aug. 30, 1993

[51] Int. Cl.⁶ .......................... C12N 15/11; C12N 15/12; C12N 15/62
[52] U.S. Cl. ...................... 536/23.5; 536/23.1; 536/23.4; 536/24.1; 536/24.31
[58] Field of Search .................................. 536/23.1, 23.4, 536/23.5, 24.1, 24.31; 435/320.21, 172.3

[56] References Cited

U.S. PATENT DOCUMENTS

| | | | |
|---|---|---|---|
| 4,952,499 | 8/1990 | Cantor | 435/172.3 |
| 4,992,367 | 2/1991 | Cullen | 435/69.52 |

FOREIGN PATENT DOCUMENTS

| | | |
|---|---|---|
| 8900194 | 1/1989 | WIPO . |

OTHER PUBLICATIONS

Nagpala et al. (1990), J. Cell Biochem., Supplement 14 part E, p. 323, abstract R330.
Novak et al. (1990), Nucl. Acids Res. 18(15):4523–4533.
J. Jaynes et al., "In vitro Cytocidal Effect of Lytic Petides on Several Transformed Mammalian Cell Lines," *Peptide Research*, pp. 157–160.
W. Reed et al., "Enhanced In Vitro Growth of Murine Fibroblast Cells and Preimplantation Embryos Cultured in Medium Supplemented with an Amphipathic Peptide," *Mol Reprod & Devel*, 31:106–113 (1992).

*Primary Examiner*—Mindy Fleisher
*Assistant Examiner*—Philip W. Carter
*Attorney, Agent, or Firm*—Trask, Britt & Rossa

[57] ABSTRACT

A DNA cassette containing sequences encoding a lytic peptide under the transcriptional control of an immune system regulating sequence is disclosed. The control sequences normally permit expression only when a defined indicator(s) reflective of a disease state is present, and tightly inhibit expression when such indicator(s) is absent. The invention further extends to transgenic unicellular and multicellular organisms having the cassette stably integrated in their genetic material. A preferred embodiment of the cassette has the Shiva-1 lytic peptide under the control of IL-2 (interleukin-2) regulating sequences. In a preferred embodiment of multicellular organisms, the cassette is incorporated into the genomes of the germ cells and the organisms are capable of transmitting it to their offspring.

20 Claims, 2 Drawing Sheets

DNA CASSETTE AND TRANSGENIC ORGANISMS CARRYING LYTIC PEPTIDE-ENCODING GENES

BACKGROUND OF THE INVENTION

1. Field

The invention relates to genetic engineering of mammals for disease resistance and to cells and animals so engineered.

2. State of the Art

The production of novel organisms by techniques of genetic engineering, including both unicellular and multicellular organisms and tissue culture cell lines, has been applied to achieve various objectives. For example, the "Harvard mouse" is a strain of mice which have been genetically altered to have increased susceptibility to the induction of cancer by damaging a particular gene. Another example is the development of a bacterial strain carrying a foreign gene which confers the ability to "eat" petroleum and related compounds on the host.

Desirably, in a genetically-engineered organism, the foreign gene should be stably present in the germ cells of the organism so that it is transmitted to its offspring and to subsequent generations of the organism. Further, it is often desirable that the process of obtaining the transgenic organism not require integration of the gene at a specific site in order for expression of the gene to occur. This makes the process more reproducible, which is particularly important when dealing with alteration of multicellular animals where the generation times are generally long compared to those of unicellular organisms.

A class of cellular polypeptides known as "lytic polypeptides" has been found to be active against various disease-causing agents including bacteria and viruses. These lytic polypeptides form complexes in the cell's outer coat or membrane, and a present hypothesis is that the complexes form pores which allow unregulated transfer of fluid and molecules across the membrane. According to this hypothesis, the cells die because of osmotic imbalances resulting from this unregulated transfer. Whatever the mechanism, the naturally occurring lytic peptides and various modified peptides having certain peptide sequence or structure in common with the naturally occurring lytic peptides have been found to have cytocidal activity against bacteria, fungi, protozoans, and various other microbial pathogens.

PCT patent publication No. WO 89/00194 (priority date U.S. patent application filed Jul. 7, 1987), by Jaynes et al., discloses numerous lytic peptides including both naturally occurring ones and modified lytic peptides. Jaynes et al. also disclose methods for treating certain cancers or infections with various prokaryotic and eukaryotic microbial pathogens by injection or the like of the lytic peptides. An earlier application by Jaynes et al., U.S. patent application Ser. No. 07/889,225 filed Jul. 25, 1986, discloses vectors for encoding certain lytic peptides and the production of disease-resistant transgenic plants containing gene sequences expressing such lytic peptides. The Jaynes applications also disclose use of lytic peptides for injection or application to a sick organism.

Quantities of lytic peptides or lytic peptide analogues sufficient for experimental use can be made on a peptide synthesizer. Also, lytic peptides have also been successfully overproduced in insect cell cultures using the baculovirus-Spodoptera expression system. Because the lytic peptides are native to these insect species, the insect cells are thus resistant to their deleterious effects.

However, so far as the present inventors are aware, no one has yet been able to achieve a disease-resistant mammalian or other non-insect vertebrate unicellular or multicellular organism having an expressible gene encoding a lytic peptide stably integrated into its genome. While Jaynes et al. were able to produce transgenic plants expressing a lytic peptide, their success is due to the difference in cell wall and membrane structures of plants, which make them insusceptible to attack by the lytic peptide. In contrast, in other prokaryotic and non-insect eukaryotic cells and animals, expression of an introduced gene for a lytic peptide can result in death or serious harm to the host cell. If the gene encoding the lytic peptide is under the control of a regulator that permits even low levels of expression, long-term growth of the host (or culture of the cell line) is difficult to achieve.

While their sensitivity is less than that of bacteria and most eukaryotic pathogens, mammalian cells are also susceptible to killing by lytic peptides. Unless the gene encoding the lytic peptide is under very tight control, leaky expression of the peptide has generally negative effects on host mammalian cells. However, if tight control is provided, one is faced with the problem of how to obtain selective and beneficial expression of the lytic peptide, otherwise, the benefits of the integrated gene cannot be realized.

Thus, a need remains for a DNA cassette and method for producing mammalian and non-insect eukaryotic transgenic organisms having a stably integrated gene encoding a lytic peptide, with the gene being selectively expressed only under conditions such as disease states where expression is desirable and without significantly jeopardizing the general hardiness and well-being of the host organisms. A need further remains for such DNA cassette and method which are useful to transfect both unicellular and multicellular organisms.

SUMMARY OF THE INVENTION

The invention comprises a DNA cassette containing sequences encoding a lytic peptide which are under the transcriptional control of regulating sequences that normally permit expression only when a defined indicator(s) reflective of a disease state is present, and which tightly inhibit expression when such indicator(s) is absent. The invention further extends to transgenic unicellular and multicellular organisms having the cassette stably integrated in their genetic material. In one preferred embodiment of multicellular organisms, the cassette is incorporated into the genomes of the germ cells and the organisms are capable of transmitting it to their offspring. In another embodiment, the cassette is incorporated into cells such as tumor-infiltrating lymphocytes or bone marrow stem cells removed from a host for transfection, and then re-introduced into the patient to provide therapeutic benefits.

In a presently preferred embodiment, the regulating sequences are sequences which allow significant expression only in certain cells and only in response to a disease or wound state. In a highly preferred embodiment, the regulating sequences are the same, or functionally similar to, those which regulate expression of interleukin-2.

Desirably, the encoded lytic peptide is one which is more toxic to selected target pathogens than to the mammalian or non-insect vertebrate host cells. In a presently preferred embodiment, the encoded lytic peptide is Shiva-1. However, other useful lytic peptides and modified lytic peptides include cecropin-B, SB-37, Anubis-1, -2, -3 and -4; Shiva-2, -3, -4, -5, -6, -7, -8, -9 and -10; melittin; and Vishnu series lytic peptides.

The unicellular organisms of the invention include mammalian tissue culture cells and cells removed from a mammalian host for temporary culture in vitro, such as bone marrow cells or tumor-infiltrating lymphocytes (TILs), prior to reintroduction into the host.

It is within contemplation that other regulating sequences may be useful in the DNA cassette. Suitable sequences would control expression of the lytic peptide such that it is expressed in tandem with a host's normal response to a disease condition, and is not "leaky" under normal conditions, e.g. there is little or no production of the lytic peptide in the absence of a disease state recognizable by the host organism. Sequences which may be useful include c-myc-regulating sequences and tumor necrosis factor-regulating sequences.

The invention further embraces methods of making the transgenic animals and cells, and methods of using cells carrying the cassette.

DETAILED DESCRIPTION OF THE PREFERRED EMBODIMENTS

Figure 1:
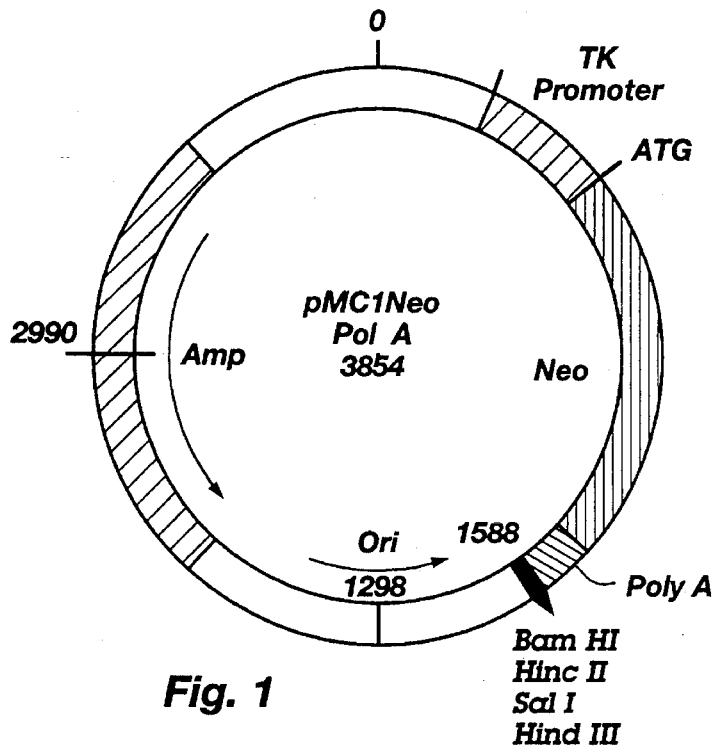
FIG. 1 depicts a general map of a commercially available plasmid carrying a NEO expression cassette useful to make the cassette of one embodiment of the invention.
Figure 2:
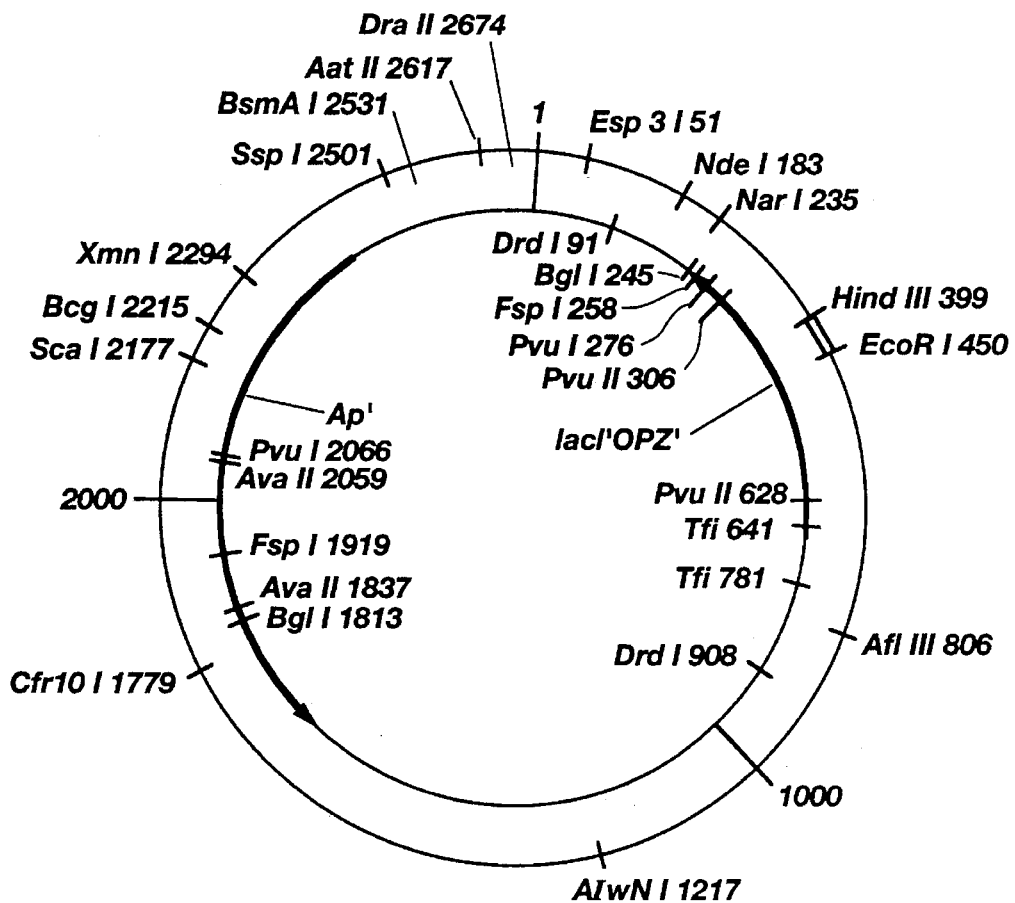
FIG. 2 depicts a general map of another plasmid used as a basis for a cassette of the invention.

In one preferred embodiment, the regulatory sequence used is that normally associated with regulation of the interleukin-2 gene. Interleukin-2 (IL-2) is a growth factor for thymus-derived lymphocytes (commonly referred to as "T cells"), and is only synthesized by "activated" T cells. Activation occurs as a result of interaction between a T cell and the surface of a macrophage, which has itself interacted with an antigen or pathogen-infected cell; it is believed that the macrophage presents an antigen to the T cell as part of this process. Activation of the T cell in turn triggers synthesis of IL-2. The IL-2 noncoding sequences (control or regulatory sequences) adjacent the IL-2 coding sequences have been determined to be required for this triggering of IL-2 synthesis upon activation of the T cell.

The regulatory region of the IL-2 gene includes a noncoding promoter sequence and a signal sequence downstream of the promoter. This signal sequence is transcribed to form a signal peptide preceding the IL-2 gene product, which helps target the gene product for secretion by a mammalian cell. The signal peptide is cleaved from the gene product within the cell and prior to secretion. To obtain the desired antimicrobial effects of the expressed lytic peptide, it is highly preferred that the lytic peptide be secreted.

Since activation of a T cell is associated with activity of the immune system in response to an actual or potential disease state, the IL-2 regulating sequences are ideal for controlling the expression of a lytic peptide. Further, as mentioned previously, IL-2 is produced only in T cells. Thus, in making a transgenic animal carrying a gene for a lytic peptide under the IL-2 regulatory control, one avoids the problem of having the lytic peptide synthesized in all tissues and potentially causing harm to the animal. In the present invention, the lytic peptide is effectively delivered primarily at the appropriate site, e.g. adjacent the pathogenic organism or in the lymphoid system where it may contact the pathogen. Also, the lytic peptide is synthesized in significant amounts only when required by the existence of a disease state which triggers activation of T cells.

A further desirable feature for regulating sequences to control expression of a lytic peptide is that they provide "tight" control of expression. By "tight" expression, it is meant that there is essentially no detectable gene product produced in the absence of the "trigger" signal. The IL-2 regulating sequences appear to regulate expression more tightly than do the regulating sequences associated with most other interleukins, with the exception of interleukin-12. Thus, the tight expression provided by the IL-2 promoter is a further advantage of the cassette for the production of transgenic organisms.

U.S. Pat. No. 4,992,367 to Cullen discusses methods and compositions for enhancing the expression of interleukin-2 in mammalian cells, involving substitution of the rat IL-2 control sequences for the "native" human IL-2 control sequences. U.S. Pat. No. 4,952,499 to Cantor et al. discloses certain other genes and gene products which regulate expression of the IL-2 receptor. This receptor is found on the surfaces of T cells, and binding of IL-2 to this highly specific receptor is part of the mechanism by which IL-2 stimulates reproduction of activated T cells.

In the instant embodiment, in which production of transgenic mice was used to demonstrate the feasibility of the invention, the interleukin-2 promoter was obtained from mouse genomic DNA using a polymerase chain reaction (PCR). A crude extract of DNA was made from Swiss Albino mouse 3T3 fibroblast cells (ATCC #CCL 92), and primers as shown in SEQ. ID#1 and #2 were used for the PCR reaction to amplify a portion of the mouse IL-2 gene from nucleotides −593 to +110. In the numbering scheme to which the aforementioned nucleotide numbers refer, "1" is taken to be the first nucleotide of the segment coding for the IL-2 protein. In the natural host organism, it is known that binding sites for NF-kappa-B, NF-AT, AP-1, AP-3 and Oct-1 are found in the region from nucleotides −593 to −1 of the complete IL-2 gene. The complete sequence of this region is on record with EMBL with accession No. X52618. In addition, in vivo in the mouse genome there is a segment between the regulatory sequences and the IL-2 coding sequence, which is a so-called "signal" sequence. This segment (from nucleotides +1 to +110 in the IL-2 gene) is transcribed and translated but is cleaved from the IL-2 protein after its passage into the endoplasmic reticulum. The signal sequence segment has been published by Fuse et al., *Nucleic Acids Res.* 12:9323 (1984).

The upstream primer (SEQ. ID #1) has a sequence complementary to the anti-sense strand (e.g., to bind to the antisense strand), while the downstream primer (SEQ. ID #2) has a sequence complementary to the sense strand. Additionally, in this embodiment there are six additional nucleotides on the upstream end of the upstream primer (SEQ. ID #1) and seven additional nucleotides on the downstream end of the downstream end which are not part of the native sequence, and which were added in order to form, respectively, SalI and BglII restriction enzyme recognition sites. These restriction sites were added to aid in cloning and placement next to the lytic peptide coding sequence to form the cassette, and for preparing the cassette for transfer into embryos. These two restriction sites were selected for convenience; others could be used if desired. The primers were of sufficient length (twenty-five nucleotides) that the short non-homologous regions at the ends did not interfere with adequate amplification of the desired IL-2-regulon sequences.

The PCR-reacted DNA was run on a gel, and a band of about 715 nucleotides in length corresponding to the expected length of the amplified fragment was isolated and identified. The amplified fragment contains the major up-regulatory, cis-acting control sequences of the 5' flanking region of the IL-2 gene, a TATA box, a PstI site at +43, the sequence encoding the 21 amino acid signal peptide, and the added SalI and BglII restriction sites. The amplified fragment was isolated from this band, made blunt-ended, and cloned into the SmaI site of pUC18 (commercially available from several suppliers, including U.S. Biochemical, Cleveland Ohio, cat. #70070; BRL Life Technologies, Gaithersburg Md., cat. #5363SA; and Boehringer Mannheim Corp., Indianapolis Ind., cat. #885797). The resulting plasmid was termed pUC-IL.

Shiva-1 is a 38-amino acid polypeptide encoded by nucleotides 777–891 of SEQ. ID #3. The sequence for Shiva-1 and for other lytic peptides and lytic peptide homologues can be found in PCT (World) patent publication no. WO 89/00194. In the present case, the Shiva-1 coding sequence was removed from plasmid pMON530 (obtained from Jaynes et al.) by digestion with BglII and EcoRI. The Shiva-1 fragment was separated by electrophoresis and purified from the gel. Plasmid pUC-IL was digested with BglII and EcoRI, and the Shiva-1 coding fragment was ligated into the gap, such that it was in frame with the signal sequence. The plasmid was tested by restriction digest analysis and by sequencing to determine that it carried the correct insert. The sequence of the complete insert is submitted as SEQ. ID #3 with this application. The plasmid containing the insert having SEQ. ID #3 is referred to as "pILSHI".

Also, a NEO expression cassette (a selectable marker conferring neomycin resistance) was taken from plasmid pMC1NeoPolA (FIG. 1; available from Stratagene, La Jolla Calif. 92037, catalog no. 213201) by cutting the plasmid with Xho I and Sal I. The fragment corresponding to the NEO cassette was then purified and subcloned into the pILSHI plasmid at the SalI site upstream of the IL-2/Shiva-1 sequences, and in reverse orientation to those sequences. The resulting plasmid is referred to as "pILSHI/neo". This plasmid contains the IL-2 promoter and signal sequences adjacent the Shiva-1 coding sequence, a fusion peptide sequence coding for three amino acids (Arg, Ser, Thr) which intervenes between the signal sequence and the Shiva-1 coding sequence, and the NEOgene under the control of the thymidine kinase promoter.

The NEO marker is optional, as it is not needed for the production of transgenic animals (multicellular organisms), but it is highly desirable for transfections into unicellular organisms such as in vitro cultured cells. Other suitable selectable markers could be used in place of NEO for the cassette.

The PILSHI or PILSHI/neo plasmid can be propagated in appropriate bacterial strains. Presently, it is being propagated in E. coli strain DH5αMCR (available from BRL, Gaithersburg, Md.), which is methylase-defective.

Figure 3:
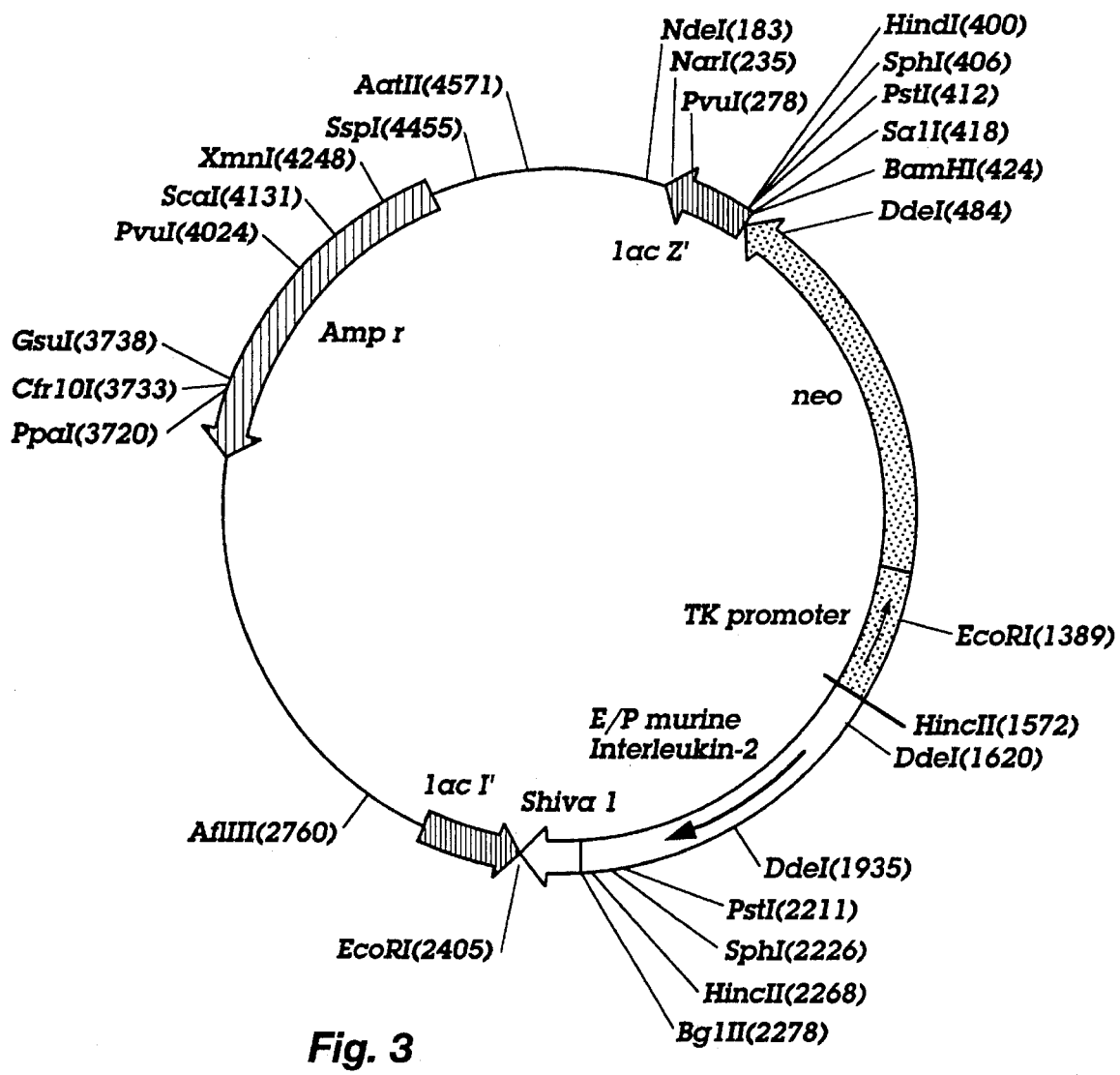
FIG. 3 depicts a map of a plasmid designated pILSHI/neo which carries an embodiment of the DNA cassette of the invention.

A cassette according to the invention may be introduced into a living host by any appropriate method. It is presently preferred to prepare the cassette DNA to a size of less than about 15 kilobases for insertion. In the embodiment of FIG. 3, this can be done by digestion with PvuI, which cuts at the indicated sites to produce a fragment which is 3746 basepairs in length. Preferably also, the fragment which carries the cassette is separated from the remaining DNA before insertion.

Insertion of the cassette into the genomes of tissue culture cells or cells and tissues removed from a host, can be performed as known in the art by electroporation, microinjection, and the like. For this purpose, the cassette desirably contains a marker permitting selection of cells which have integrated the cassette, such as the neomycin resistance gene commonly known as NEO.

Insertion of the cassette into the genome of a multicellular organism may be accomplished by injection into early embryos. For this purpose, the cassette need not contain a selection marker. It is highly desirable that the cassette be integrated into the genome of the germ cells, so that the cassette will be transmitted to subsequent generations stemming from the original engineered organism. It will generally be necessary to screen the animals which result from the injected embryos to ascertain which have the cassette in their DNA. It may further be desirable to screen either selected tissues or the first generation offspring of the engineered animals, to determine whether the cassette is present in the germline cells.

In an alternate embodiment, the regulatory segment may be the c-myc promoter. The c-myc gene is also selectively expressed in certain cells and in response to disease and wound-related conditions. For example, c-myc is expressed in activated T cells (like IL-2) and in fibroblasts at wound sites. Its expression is also stimulated by growth factors.

Lytic peptides (when present at low and non-toxic levels) also have the property of stimulating proliferation in mammalian and other cells. Thus, the selective expression of lytic peptides in a wound is expected to speed healing of the wound in addition to preventing infection in the area. The sequence for the c-myc gene has been determined and is available under accession #L00038 from EMBL.

In a further embodiment specifically directed at improved wound-healing or stimulation of cell growth, the cassette comprises the c-myc promoter linked to Vishnu-1 or a lytic peptide analogue having similar properties. Vishnu-1 is a truncated version of Shiva-1 which lacks the cytolytic and toxic properties of Shiva-1, but still induces proliferation of mammalian and bacterial cells.

EXAMPLE 2

Production of Transgenic Mouse Carrying the Cassette

Preparation of DNA for Injection into Embryos

A PvuI restriction enzyme digest of pILSHI/neo was performed to linearize the DNA and remove a portion of the vector not required for mammalian cell expression. The fragment was purified by agarose gel electrophoresis and separated from the gel slice using GeneClean (Bio 101, La Jolla, Calif., 92038-2284). The DNA was eluted from the glass beads using 10 μL of injection buffer (10 mM tris, 0.15 mM EDTA, pH 7.4). The solution was then dialyzed through a 0.025 μm pore size mixed esters of cellulose filter membrane (Millipore, Bedford, Mass., 91013) against three changes of a 10 mL pool of injection buffer over 72 h. The DNA concentration of the recovered solution was determined by staining with ethidium bromide and comparing against standards, then the concentration of the solution was adjusted to 2.5 ng/μL.

Preparation and Microinjection of Embryos and Transfer into Recipient Females

Twenty-five six-week old female mice of strain B6SJLF1/J (Jackson Laboratory) were used as embryo donors. Twelve hours before the midpoint of the daily dark cycle, they were given intraperitoneal (IP) injections of seven IU (International Units) of pregnant mare serum gonadotropin (PMSG). Forty-seven hours later, the mice were given IP injections of 7 IU of human chorionic gonadotropin (hCG). Immediately after the hCG injections, they were transferred to cages containing proven fertile males of the same strain. No more than two females were in with each male. The donor females were left with the males for 22 hours, then removed and checked for a vaginal plug. Those with plugs were humanely killed, and the reproductive tract was removed and washed in M2 medium. Embryos were released from the ampullar region of the oviduct of these uteri into M2 medium. The embryos were washed in fresh medium, then transferred to M2 medium containing 1 mg/ml hyaluronidase and flushed gently within a small bore pipet to remove cumulus cells. They were then transferred to M2 medium without hyaluronidase, and placed in an incubator at 37° C., 5% $CO_2$ in air atmosphere, to await microinjection and transfer.

Forty-five six and eight week old CD1 (Jackson Laboratory) and FVB/N (Teconic Labs) female mice were used as the recipient females. The same hormone protocol described for preparation of the donor females, was used to prepare the recipient females. The prepared recipient females were induced to pseudopregnancy by mating with vasectomized males (strain C57/B).

As quickly as possible following removal from the donor females, an aliquot of the DNA solution (see above) was microinjected into the pronucleus of each embryo. The microinjected embryos were then transferred into the oviduct of congenic female mice. Microinjection into the pronucleus was performed basically as described by Allen et al. (in: *Mammalian Development*, a practical approach, M. Monk, editor, Irl Press, Oxford, England, 1987). On the average, the time the embryos were in M2 medium in the incubator, was generally around 40 min prior to microinjection and 15 to 60 minutes between micro-injection and transfer into recipient females, for a total of about 1–2 hours. Manipulations were carried out at room temperature in air.

Injected embryos were transferred using a glass pipette to the oviducts of recipient females anesthetized with tribromoethanol (Avertin), through bilateral flank incisions. Ten to fifteen embryos were transferred to each side. A total of ten recipients were used, of which three delivered live litters at normal gestational term. Nineteen pups survived to weaning at three weeks of age.

EXAMPLE 3

Screening for Transgenic Animals

A PCR reaction using mouse tail DNA as template and primers which amplify both native interleukin-2 promoter and the IL2/Shiva 1/neo introduced fragment was performed as the primary detection technique.

At weaning, a 1.5 cm length of tissue was cut from the end of each pup's tail and digested overnight in Tail Extraction Buffer (100 mM tris, 5 mM EDTA, 0.2%SDS, 200 mM NaCl, 0.1 mg/mL proteinase K as described by R. Huntress, DNX Inc.). Hair and other undigested tissue were pelletted and the supernatant transferred to a fresh tube containing two volumes of ethanol. Precipitation was carried out over night at 20° C., the precipitate pelletted by centrifugation, and the dried pellet resuspended in 200 μL of TE buffer (10 mM tris, 1 mM EDTA, pH 7.6).

One microliter of the mouse tail DNA solution was added to the standard reaction described by Perkin Elmer Cetus (Norwalk, CN, 06859) and 40 pMol of a primer for the interleukin-2 5'-flanking region, TAGATCTTGCGCTGT-TGACAAGGAG (Seq. ID #2); 20 pMol of a primer for the interleukin-2 signal sequence, AGTCGACAACGA-CAAAATAGTACCT (Seq. ID #1); and 20 pMol of a primer for the coding region of the NEO gene, CCACCATGATAT-TCGGCAAGC. This combination amplifies two regions of transgenic mouse genomic DNA but only one of native mouse DNA. To increase the sensitivity of the detection, a Southern blot was performed as directed in the instructions for the Polar Plex Chemileuminescent Blotting Kit (Millipore) using whole linearized pILSHI/neo plasmid labeled with biotin as a probe. Of the 19 mouse pups tested, one tested positive for the transgene.

The cassette of the invention is useful for numerous purposes. First, it may be used to produce transgenic animals which have resistance to disease, particularly to organisms which are susceptible to killing by lytic peptides. Such a disease-resistant trait would be useful in cows, sheep, pigs, chickens, and other domestic animals, as it would reduce the frequency and severity of common bacterial, fungal and protozoan infections. Since lytic peptides can also attack mammalian cells infected by some viruses, viral infections could also be mitigated. The reduction in infections would contribute to faster growth of animals to market size and lower veterinary costs for farmers who raised such disease-resistant animals.

The cassette is also useful to transform cells removed from a diseased human patient or animal, so that upon re-introduction into the patient, disease resistance may be enhanced or a particular disease treated. For example, tumor-infiltrating lymphocytes (TILs) can be recovered from a patient's own tumor, transfected in vitro with the cassette, and reintroduced into the host. TILs selectively migrate into tumor tissue and are known to produce high levels of IL-2. Lytic peptides and lytic peptide analogues are known to have selective cytocidal activity against tumor cells. Various lytic peptides and lytic peptide analogues are known to differ in their effectiveness against fungi, protozoa, and tumor cells. For example, melittin is believed to be particularly effective against tumor cells and thus may be preferred for transfection of TILs.

An advantage of the cassette is that, since it provides its own regulating sequences, the probability of success using random integration techniques is generally high. Further, the types of regulating sequences used ensure that the expression of the lytic peptide or l.p. analogue is substantially limited to circumstances where it is desirable, e.g. conditions where an infection or a wound exists. Lytic peptide expression is further limited to certain cell types which are targeted to the infection or wound site. Injury to the host by production of the lytic peptide when it is not needed, is avoided.

What is claimed is:

1. A DNA cassette for insertion into non-insect animal cells, having opposing ends whose sequences encode a functional portion of a restriction cut site, comprising:
   a regulatory segment having a sequence which is a noncoding sequence normally found adjacent to, and operably linked to, a gene which codes for an interleukin protein, or a functional homologue of said noncoding sequence; and
   a lytic peptide segment coding on expression for a lytic peptide and operably linked to said regulatory segment for control of expression by said regulatory segment.

2. The cassette of claim 1, wherein said interleukin protein is selected from the group consisting of interleukin-2, and interleukin-12.

3. The cassette of claim 1, wherein said lytic peptide is selected from the group consisting of: SB-37, cecropin B, Shiva-1, Shiva-2, Shiva-3, Shiva-4, Shiva-5, Shiva-6, Shiva-7, Shiva-8, Shiva-9, and Shiva-10.

4. The cassette of claim 3, wherein said lytic peptide is Shiva-1.

5. The cassette of claim 2, wherein said lytic peptide is selected from the group consisting of: SB-37, cecropin B, Shiva-1, Shiva-2, Shiva-3, Shiva-4, Shiva-5, Shiva-6, Shiva-7, Shiva-8, Shiva-9, and Shiva-10.

6. The cassette of claim 5, wherein said lytic peptide is Shiva-1.

7. The cassette of claim 1, wherein said regulatory segment causes expression to selectively occur in tandem with activation of T lymphocytes.

8. The cassette of claim 7, wherein said lytic peptide is selected from the group consisting of: cecropin B, functional analogs of cecropin B, SB 37, Shiva series lytic peptide analogs, and Vishnu series lytic peptide analogs.

9. The cassette of claim 8, wherein said interleukin protein is IL-2 or IL-12.

10. The cassette of claim 9, wherein said lytic peptide is Shiva-1.

11. The cassette of claim 1, wherein said regulatory segment substantially limits expression of said interleukin protein to cells of a lymphoid lineage.

12. The cassette of claim 11, wherein said interleukin protein is IL-2 or IL-12.

13. The cassette of claim 12, wherein said lytic peptide is Shiva-1.

14. The cassette of claim 1, wherein said regulatory segment causes expression to selectively occur in response to activation of T cells, and said lytic peptide is selected from the group consisting of: cecropin B, functional analogs of cecropin B, SB 37, Shiva series lytic peptide analogs, and Vishnu series lytic peptide analogs.

15. The cassette of claim 14, which further includes a secretion signal sequence operably connected to said lytic peptide coding sequence to cause a lytic peptide synthesized therefrom to be secreted from a cell.

16. The cassette of claim 15, wherein said regulatory segment normally regulates the expression of a protein selected from the group consisting of interleukin 2 and interleukin-12.

17. The cassette of claim 1, which has opposing ends constructed for insertion into genomic DNA of a host mammal.

18. The cassette of claim 1, wherein said regulatory segment induces expression in response to conditions which cause activation of T lymphocytes.

19. A DNA cassette having opposing ends constructed for insertion into genomic DNA of a host mammalian cell, comprising:

a noncoding regulatory sequence normally found adjacent to, and operably linked to, a gene encoding an interleukin protein selected from the group consisting of IL-2 and IL-12, or a functional homologue of said regulatory sequence; and a lytic peptide segment coding on expression for a lytic peptide and operably linked to said regulatory sequence for control of expression by said regulatory sequence.

20. The DNA cassette of claim 19, wherein said lytic peptide segment codes on expression for Shiva-1.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mouse
        ( B ) STRAIN: 3T3 Swiss albino ( x i ) SEQUENCE DESCRIPTION: SEQ ID NO:1:

```
AGTCGACAAC GACAAAATAG TACCT                                              25
```

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mouse
        ( B ) STRAIN: 3T3 Swiss albino ( x i ) SEQUENCE DESCRIPTION: SEQ ID NO:2:

```
TAGATCTTGC GCTGTTGACA AGGAG                                              25
```

( 2 ) INFORMATION FOR SEQ ID NO:3:

( i ) SEQUENCE CHARACTERISTICS:
        ( A ) LENGTH: 932 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Mouse
        ( B ) STRAIN: 3T3 Swiss albino ( x i ) SEQUENCE DESCRIPTION: SEQ ID NO:3:

```
GTAAAACGAC  GGCCAGTGCC  AAGCTTGCAT  GCCTGCAGGT  CGACTCTAGA  GGATCCCCAG      60
TCGACAACGA  CAAAATAGTA  CCTCAAGCTC  AACAAGCATT  TTAGGTGTCC  TTAGCTTACT     120
ATTTCTCTGG  CTAACTGTAT  GAAGCCATCT  ATCACCCTGT  GTGCAATTAG  CTCATTGTGT     180
AGATAAGAAG  GTAAAACCAT  CTTGAAACAG  GAACCAATA   TCCTTCCTGT  CTAATCAACA     240
AATCTAAAAG  ATTTATTCTT  TTCATCTATC  TCCTCTTGCG  TTTGTCCACC  ACAACAGGCT     300
GCTTACAGGT  TCAGGATGGT  TTTGACAAAG  AGAACATTTT  CATGAGTTAC  TTTTGTGTCT     360
CCACCCCAAA  GAGGAAAATT  TGTTTCATAC  AGAAGGCGTT  CATTGTATGA  ATTAAAACTG     420
CCACCTAAGT  GTGGGCTAAC  CCGACCAAGA  GGGATTTCAC  CTAAATCCAT  TCAGTCAGTG     480
TATGGGGGTT  TAAAGAAATT  CCAGAGAGTC  ATCAGAAGAG  GAAAAACAAA  GGTAATGCTT     540
```

| | | | | | | |
|---|---|---|---|---|---|---|
| TCTGCCACAC | AGGTAGACTC | TTTGAAAATA | TGTGTAATAT | GTAAAACATC | GTGACACCCC | 600 |
| CATATTATTT | TTCCAGCATT | AACAGTATAA | ATTGCCTCCC | ATGCTGAAGA | GCTGCCTATC | 660 |
| ACCCTTGCTA | ATCACTCCTC | ACAGTGACCT | CAAGTCCTGC | AGGCATGTAC | AGCATGCAGC | 720 |
| TCGCATCCTG | TGTCACATTG | ACACTTGTGC | TCCTTGTCAA | CAGCGCAAGA | TCTACCATGC | 780 |
| CGCGCTGGCG | TCTGTTCCGC | CGTATCGACC | GTGTTGGCAA | ACAGATCAAA | CAGGGTATCC | 840 |
| TGCCGTGCTG | GCCCGGCTAT | CGCTCTGGTT | GGCGACGCCC | GCGCAGTTGG | TTGAGAATTC | 900 |
| GTAATCATGG | TCATAGCTGT | TTCCTGTGTG | AA | | | 932 |

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: double
( D ) TOPOLOGY: unknown ( i i ) MOLECULE TYPE: DNA (genomic)

( i i i ) HYPOTHETICAL: NO ( v i ) ORIGINAL SOURCE:
( A ) ORGANISM: Streptomyces fradiae ( x i ) SEQUENCE DESCRIPTION: SEQ ID NO:4:

CCACCATGAT ATTCGGCAAG C          21